United States Patent
Stonefield et al.

(10) Patent No.: US 9,129,048 B2
(45) Date of Patent: Sep. 8, 2015

(54) SYSTEMS AND METHODS FOR AN ULTRASOUND WORKFLOW

(75) Inventors: Andrew David Stonefield, Whitefish Bay, WI (US); Menachem Halmann, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 249 days.

(21) Appl. No.: 13/605,500

(22) Filed: Sep. 6, 2012

(65) Prior Publication Data

US 2014/0066766 A1  Mar. 6, 2014

(51) Int. Cl.
- G09G 5/02 (2006.01)
- G06F 19/00 (2011.01)
- A61B 8/00 (2006.01)

(52) U.S. Cl.
CPC ............ *G06F 19/3406* (2013.01); *A61B 8/463* (2013.01); *A61B 8/469* (2013.01); *A61B 8/54* (2013.01); *G06F 19/321* (2013.01); *A61B 8/4405* (2013.01); *A61B 8/4427* (2013.01)

(58) Field of Classification Search
None
See application file for complete search history.

(56) References Cited

U.S. PATENT DOCUMENTS

| | | | |
|---|---|---|---|
| 2003/0013959 A1* | 1/2003 | Grunwald et al. | 600/437 |
| 2008/0221834 A1* | 9/2008 | Damodharan | 702/183 |
| 2009/0131793 A1* | 5/2009 | Stonefield et al. | 600/443 |
| 2010/0053213 A1* | 3/2010 | Ishida et al. | 345/629 |
| 2011/0219296 A1* | 9/2011 | Michaud et al. | 715/234 |
| 2013/0232446 A1* | 9/2013 | Lin | 715/810 |

* cited by examiner

*Primary Examiner* — David Zarka
*Assistant Examiner* — Khoa Vu
(74) *Attorney, Agent, or Firm* — Dean D. Small; The Small Patent Law Group, LLC

(57) ABSTRACT

An ultrasound imaging system including a user interface configured to receive user inputs from an operator during an imaging session. The user interface includes a display device having a display area and an image-processing module that is configured to receive ultrasound signals from a diagnostic probe and process the signals to generate ultrasound images. The system also includes a workflow module that is configured to display, concurrently, an acquired image of the ultrasound images and a user-selectable element in the display area. The acquired image includes an anatomical feature of a subject. The workflow module is configured to display an activated frame over the acquired image in the display area when the user-selectable element is selected by the operator. The activated frame appears partially transparent such that the anatomical feature is visible through the activated frame.

25 Claims, 6 Drawing Sheets

SYSTEMS AND METHODS FOR AN ULTRASOUND WORKFLOW

BACKGROUND

The subject matter disclosed herein relates generally to medical imaging systems, and more particularly to workflows for operating ultrasound imaging systems.

An ultrasound imaging system typically includes an ultrasound probe that is applied to a patient's body and a workstation or device that is operably coupled to the probe. The probe may be controlled by an operator of the system and is configured to transmit and receive ultrasound signals that are processed into an ultrasound image by the workstation or device. The workstation or device may show the ultrasound images through a display device. During an imaging session, the operator typically views an imaging screen, which includes an ultrasound image. For instance, the ultrasound image may be in real-time, a recorded cine movie, or an ultrasound still frame. For some imaging sessions, the operator may switch between different screens on the display device. For instance, the operator may exit the imaging screen and open another screen to (a) enter information or data relating to the imaging session (e.g., patient data, comments regarding an ultrasound image, etc.); (b) change the settings of the probe (e.g., frequency, depth, mode, etc.); or (e) change the settings of the display or how the information is displayed to the operator (e.g., user preferences).

However, in the above examples, the operator's awareness of the ultrasound image and/or location in the workflow may be disrupted such that the operator needs more time to re-establish where he or she is in the workflow. Such disruptions may increase the overall time of the imaging session and may also increase the operator's frustration in using the ultrasound system. In some cases, the operator may not know how to return to the imaging screen, which may cause even greater delays.

BRIEF DESCRIPTION

In one embodiment, an ultrasound imaging system is provided that includes a user interface configured to receive user inputs from an operator during an imaging session. The user interface includes a display device having a display area and an image-processing module that is configured to receive ultrasound signals from a diagnostic probe and process the signals to generate ultrasound images. The system also includes a workflow module that is configured to display, concurrently, an acquired image of the ultrasound images and a user-selectable element in the display area. The acquired image includes an anatomical feature of a subject. The workflow module is configured to display an activated frame over the acquired image in the display area when the user-selectable element is selected by the operator. The activated frame appears partially transparent such that the anatomical feature is visible through the activated frame.

In another embodiment, a method of imaging a subject using an ultrasound imaging system is provided. The method includes processing ultrasound signals to generate ultrasound images. The ultrasound images include an acquired image. The acquired image includes an anatomical feature of a subject. The method also includes concurrently displaying the acquired image and a user-selectable element in a display area. The method also includes displaying an activated frame over the acquired image in the display area when the user-selectable element is selected by the operator. The activated frame appears partially transparent such that the anatomical feature is visible through the activated frame.

In yet another embodiment, a tangible non-transitory computer readable medium is provided that is programmed to instruct a computing system to process ultrasound signals to generate ultrasound images. The ultrasound images include an acquired image. The acquired image includes an anatomical feature of a subject. The computing system is also instructed to generate a display area that is configured to be displayed by a user interface. The display area includes, concurrently, the acquired image and a user-selectable element. The display area includes an activated frame that appears over the acquired image when the user-selectable element is selected. The activated frame appears partially transparent such that the anatomical feature is visible through the activated frame.

DETAILED DESCRIPTION

Figure 1:
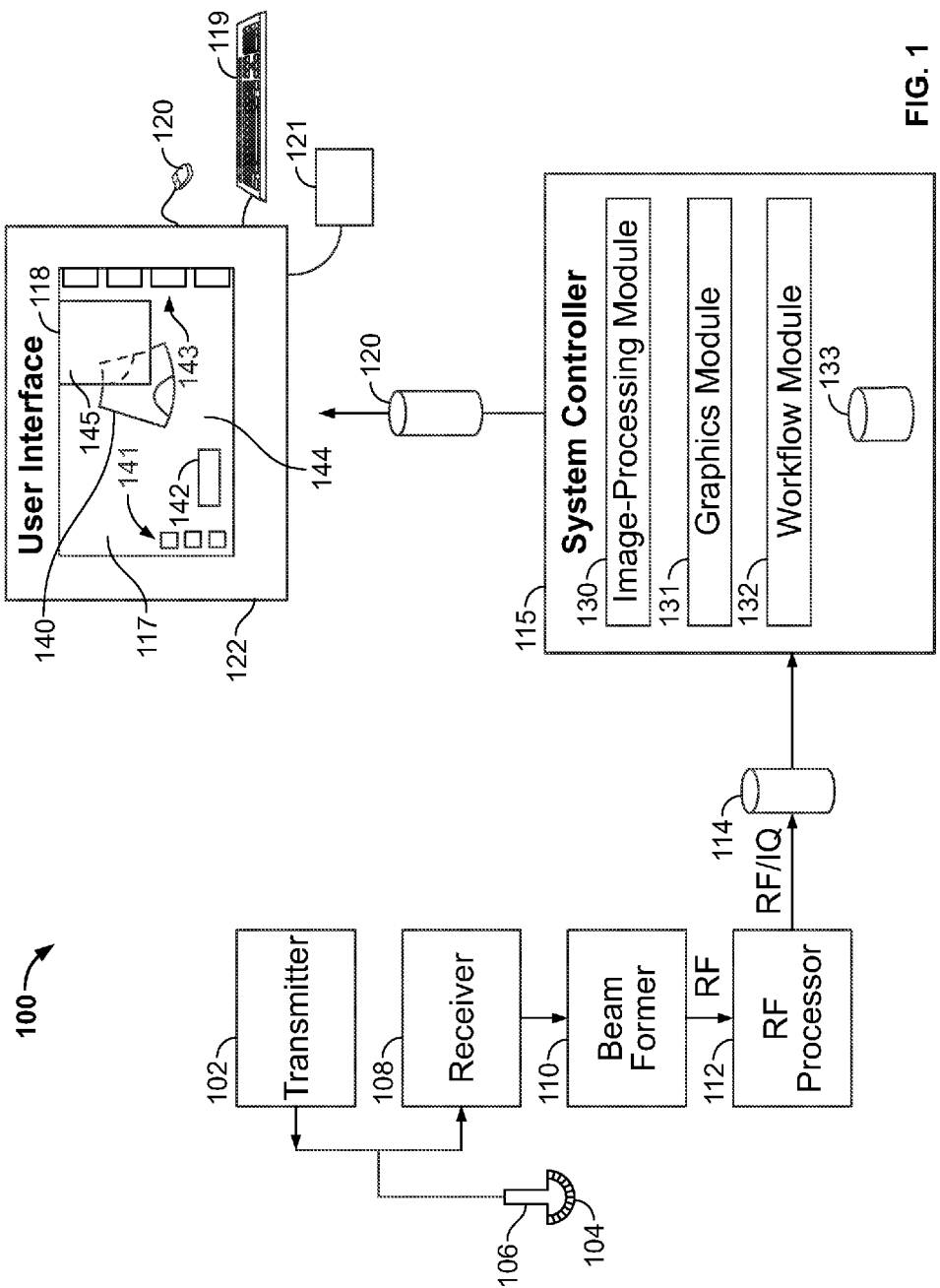
FIG. 1 illustrates a block diagram of an ultrasound imaging system in accordance with one embodiment.

Embodiments described herein include systems, methods, and computer readable media that may provide an improved workflow for acquiring medical images. For example, embodiments described herein may utilize a user interface that is configured to receive user inputs from an operator (e.g., doctor, nurse, technician, or other suitable person). When the operator is interacting with the user interface (e.g., entering data, operating a mouse or other input device, touching a screen), the user interface may enable a workflow that is less disruptive and/or smoother for the operator. For example, the user interface may display an ultrasound image while the operator is interacting with a partially transparent (e.g., translucent) window, panel, or frame so that the operator may continue to be aware or otherwise cognizant of the ultrasound image.

The following detailed description of various embodiments will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., modules, processors, or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

FIG. 1 illustrates a block diagram of an ultrasound system 100 according to one embodiment. The ultrasound system 100 may be a unitary apparatus such that the elements and components of the system 100 may be carried or moved with each other. The ultrasound systems 300, 350, 400 shown in FIGS. 4, 5, and 6, respectively, illustrate examples of such systems. However, in other embodiments, at least one of the system components and elements described herein may be located remotely with respect to other components and elements. For example, one or more of the described modules may operate in a data server that has a distinct and remote location with respect to an ultrasound probe and the user interface.

In the illustrated embodiment, the ultrasound system 100 includes a transmitter 102 that drives an array of elements 104, for example, piezoelectric crystals, within a diagnostic ultrasound probe 106 (or transducer) to emit pulsed ultrasonic signals into a body or volume (not shown) of a subject. The elements 104 and the probe 106 may have a variety of geometries. The ultrasonic signals are back-scattered from structures in the body, for example, blood cells or muscular tissue, to produce echoes that return to the elements 104. The echoes are received by a receiver 108. The received echoes are provided to a beamformer 110 that performs beamforming and outputs an RF signal. The RF signal is then provided to an RF processor 112 that processes the RF signal. Alternatively, the RF processor 112 may include a complex demodulator (not shown) that demodulates the RF signal to form IQ data pairs representative of the echo signals. The RF or IQ signal data may then be provided directly to a memory 114 for storage (for example, temporary storage). In the illustrated embodiment, the probe 106 is only configured for imaging. In other embodiments, the probe 106 may also be configured to provide therapy through, for example, high-intensity focused ultrasound (HIFU).

The ultrasound system 100 also includes a system controller 115 that includes a plurality of modules. The system controller 115 is configured to control operation of the ultrasound system 100. For example, the system controller 115 may include an image-processing module 130 that receives the ultrasound signals (for example, RF signal data or IQ data pairs) and processes the ultrasound signals to generate frames of ultrasound information (e.g., ultrasound images) for displaying to the operator. The image-processing module 130 may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. The generated ultrasound images may be two-dimensional (2D) or three-dimensional (3D).

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed frames of acquired ultrasound information that are not scheduled to be displayed immediately. The image memory 120 may comprise any known data storage medium, for example, a permanent storage medium, removable storage medium, and the like.

In operation, the ultrasound system 100 acquires data, for example, volumetric data sets by various techniques (for example, 3D scanning, real-time 3D imaging, volume scanning, 2D scanning with transducers having positioning sensors, freehand scanning using a voxel correlation technique, scanning using 2D or matrix array transducers, and the like). Ultrasound images are displayed to the operator or user of the ultrasound system 100 on the display device 118.

The system controller 115 is operably connected to a user interface 122 that enables an operator to control at least some of the operations of the image-processing module 130. The user interface 122 may include hardware, firmware, software, or a combination thereof that enables an individual (e.g., an operator) to directly or indirectly control operation of the ultrasound system 100 and the various components thereof. As shown, the user interface 122 includes a display device 118 having a display area 117. In some embodiments, the user interface 122 may also include one or more input devices, such as a physical keyboard 119, mouse 120, and/or touchpad 121. In an exemplary embodiment, the display device 118 is a touch-sensitive display (e.g., touchscreen) that can detect a presence of a touch from the operator on the display area 117 and can also identify a location of the touch in the display area 117. The touch may be applied by, for example, at least one of an individual's hand, glove, stylus, or the like. As such, the touch-sensitive display may also be characterized as an input device that is configured to receive inputs from the operator. The display device 118 also communicates information to the operator by displaying the information to the operator. The display device 118 and/or the user interface 122 may also communicative audibly. The display device 118 is configured to present information to the operator during the imaging session. The information presented may include ultrasound images, graphical elements, user-selectable elements, and other information (e.g., administrative information, personal information of the patient, and the like).

The system controller 115 also includes a graphics module 131, a workflow module 132, and a database 133. The image-processing module 130, the graphics module 131, and the workflow module 132 coordinate with one another to present information to the operator during the imaging session. For example, the image-processing module 130 may be configured to display an acquired image 140 on the display device 118, and the graphics module 131 may be configured to display designated graphics along with the ultrasound images. The graphics may include icons 141, data fields 142, user-selectable elements 143, and the like.

The workflow module 132 may be configured to guide and assist the operator during the imaging session by showing various screen configurations for different stages of the imaging session. For example, FIG. 1 illustrates an imaging screen 144. During an imaging stage, the workflow module 132 may request or receive the acquired image 140 from the image-processing module, the appropriate graphics from the graphics module 131, and the appropriate information from the database 133 to display. In FIG. 1, the imaging screen 144 includes the ultrasound image 140, the icons 141, and the user-selectable elements 143. The workflow module 132 may determine an overall layout for the display area 117 using the information provided by the other modules.

As will be described in greater detail below, in some embodiments, the operator is enabled to activate one of the user-selectable elements 143 so that an activated frame 145 appears over the imaging screen 144. The activated frame 145 may be partially transparent such that one or more portions of the acquired image 140 may be viewed through the activated frame 145. For instance, an anatomical feature or structure (e.g., bone, soft tissue, organs, fatty tissue, a chamber or space defined by the above, etc.) may be viewed through the activated frame 145. In some cases, the activated frame 145 may have regions with different transparency levels such that the anatomical feature is easier to see through a first region, but not easier to see in a second region. As such, the operator may remain aware or may be more cognizant of the acquired image 140 while executing other operations, such as entering patient data or reconfiguring the settings of the probe or the display settings, which information is also displayed in the display area 117.

Figure 2:
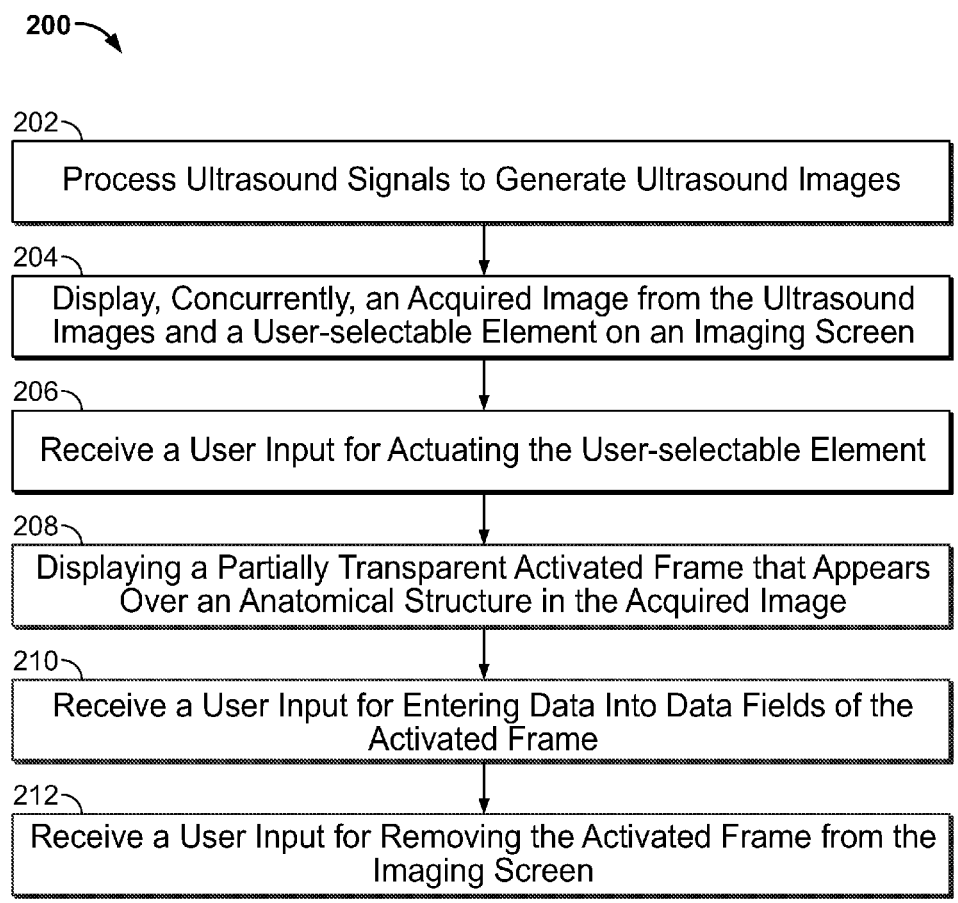
FIG. 2 is a flowchart of a method according to one embodiment.
Figure 3:
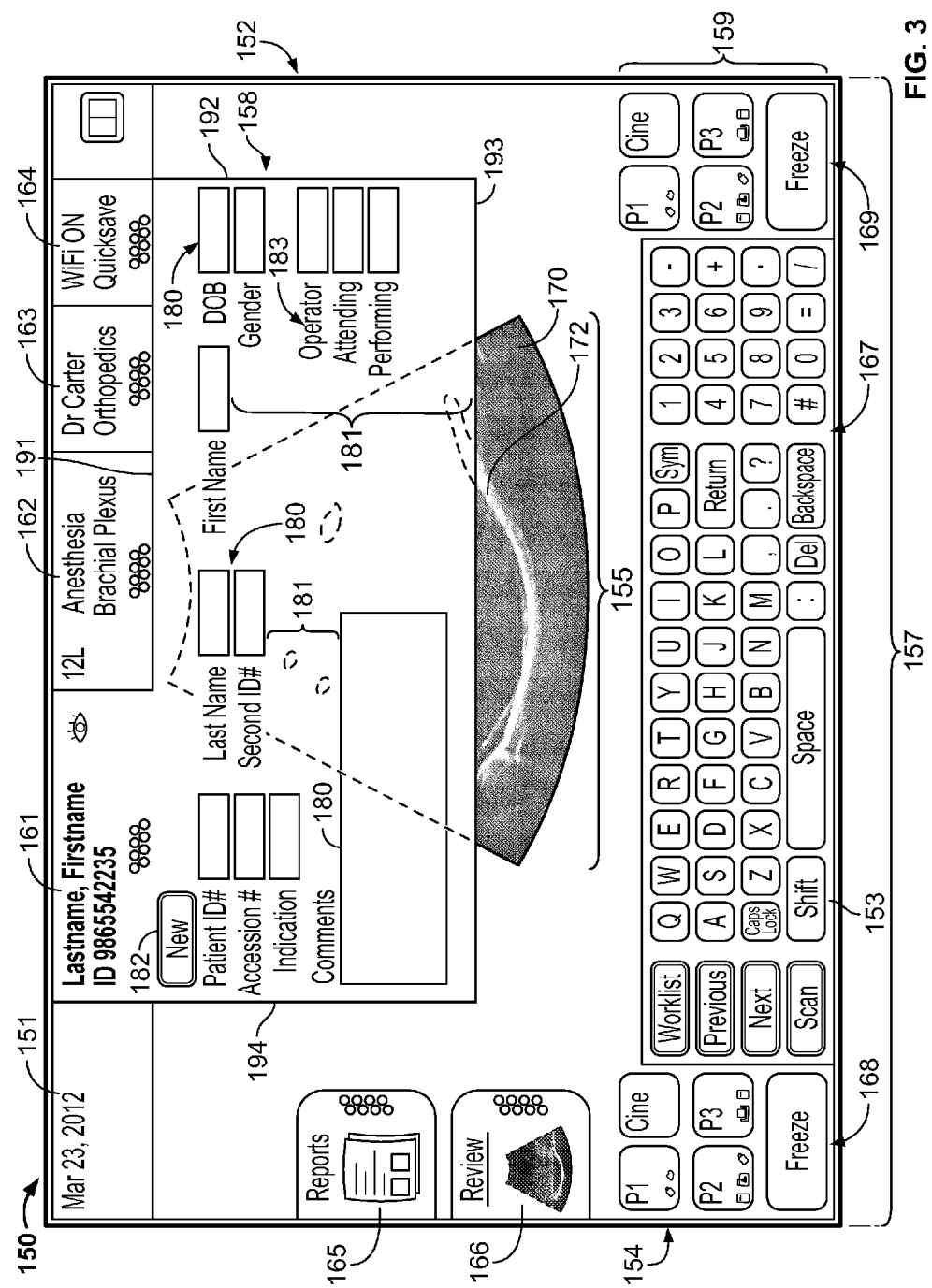
FIG. 3 illustrates a display area of a display device that may be shown by the ultrasound system of FIG. 1.

FIG. 2 is a flowchart of a method 200 of imaging a subject using an ultrasound imaging system, such as the ultrasound systems 100, 300, 350, and 400 (FIGS. 1, 4, 5, and 6, respectively). FIG. 3 is referenced in relation to the description of the method 200 and illustrates an imaging screen 150 that may be displayed to the operator while acquiring ultrasound images of the subject. The imaging screen 150 may be one of various screens that an operator may view during the imaging session. For example, the workflow module 132 (FIG. 1) may guide or allow the operator to view other screens for administrative purposes during the imaging session.

The display device 118 (FIG. 1) may include a plurality of sides or edges 151-154 that define a display area 157. The display area 157 may define an entirety of a visible area of the display device 118. The display area 157 may be defined by an array of pixels that are illuminated in a designated manner by the system controller 115 to present information to the operator. As shown in FIG. 3, the display area 157 includes an imaging screen 150 that may use an entirety of the display area 157. In other embodiments, the imaging screen 150 may use only a portion of the available area. More specifically, one or more of the dimensions (e.g., height, width) of the imaging screen 150 may be less than the corresponding dimension(s) of the display area 157. In the illustrated embodiment, a portion of the display area 157 may define an image region or area 155 where an acquired image 170 is shown and a utility region 159 (or non-image region) where the acquired image 170 is not shown. As illustrated in FIG. 3, an activated frame 158 appears over the acquired image 156.

The imaging screen 150 may also include user-selectable elements 161-169. As used herein, a "user-selectable element" includes an identifiable element or component that is configured to be activated by the operator to instruct the ultrasound system 100 to execute a desired action. The user-selectable element may be a physical element. For example, a user-selectable element may include or be part of an input device, such as a keyboard or keypad, or the user-selectable element may be a graphical-user-interface (GUI) element (e.g., a virtual element) that is displayed on an imaging screen. In the illustrated embodiment, the user-selectable elements 161-169 are virtual elements that are displayed in the imaging screen 150.

User-selectable elements are configured to be activated (or actuated) by an operator during the imaging session. Activation of the user-selectable element may be accomplished in various manners. For example, in embodiments that utilize a touch-sensitive display, the operator may press the display area 117 to activate a virtual user-selectable element. Alternatively or in addition to, the operator may select the virtual user-selectable elements using a stylus, a mouse, keys of a keyboard, voice-activation, and the like. Physical user-selectable elements may be physically activated (e.g., a button on a console may be pressed by the operator).

In some embodiments, the user-selectable element may appear as a key of a virtual keyboard, a virtual tab, a virtual switch, a virtual lever, a drop-down menu that provides a list of selections, a graphical icon, and the like. In some embodiments, the user-selectable element is labeled or otherwise differentiated (e.g., by drawing or unique shape) with respect to other user-selectable elements. When a user-selectable element is activated by an operator, signals are communicated to the system controller 115 (e.g., the workflow module 132) that indicate the operator has selected and activated the user-selectable element and, as such, desires a predetermined action. The signals may instruct the system controller 115 to act or respond in a predetermined manner.

For the embodiment shown in FIG. 3, the user-selectable elements 161-164 appear as tabs along the side 151, and the user-selectable elements 165, 166 appear as tabs along the side 154. The user-selectable elements 168, 169 appear as buttons at bottom corners of the imaging screen 150 formed by the sides 152-154. The user-selectable element 167 is a virtual keyboard having a QWERTY layout that is located in the utility region 159 proximate to the side 153.

The method 200 may include processing at 202 ultrasound signals to generate ultrasound images. As described above, the ultrasound signals may be processed with respect to various ultrasound modalities, including color-flow, ARFI, B-mode, mode, A-mode, M-mode, spectral Doppler, acoustic streaming, tissue Doppler module, C-scan, and elastography. The ultrasound images may be 2D or 3D. In some embodiments, the ultrasound images may be modified prior to being displayed (e.g., to enhance edges, enhance designated portions of an anatomical feature, add markers to the image, etc.).

At 204, the acquired image 170 from the ultrasound images and one or more of the user-selectable elements 160-169 may be concurrently displayed on the imaging screen 150. The acquired image 170 may include an anatomical feature 172 (e.g., bone, soft tissue, organs, fatty tissue, a chamber or space defined by the above, etc.) of the subject. In some embodiments, the acquired image 170 may be at least one of a single ultrasound image frame, real-time ultrasound images, or a recorded cine movie. More than one acquired image may be shown. For example, a first acquired image may include an anatomical feature before therapy and a second (e.g., real-time) ultrasound image may include the anatomical feature after therapy. The acquired image 170 may have various additions or modifications when displayed in the imaging screen 150. For example, the acquired image 170 may include markers that indicate a portion of the anatomical structure.

The method 200 also includes receiving at 206 user inputs for actuating one of the user-selectable elements and displaying at 208 the partially transparent activated frame 158 over an anatomical structure 172 of the acquired image 170. In the illustrated embodiment, the activated frame 158 appears when the display device 118 is touched by the operator at an area corresponding to the user-selectable element 161. However, the user-selectable element 161 may be selected or actuated in other manners, such as those described above.

As used herein, an activated "frame," "window," "panel," or "tray" includes a graphical element that may appear to be positioned over another graphical element in the display area. In particular embodiments, the activated frame (or like terms) comprises only a portion of the display area. The portion of the display area defined by the activated frame may appear different from the remainder of the display area such that the activated frame may be visually differentiated or distinguished from other graphical elements. For example, the activated frame 158 may have edges 191-194. A light intensity and/or color of the area defined by the edges 191-194 may be different than the surrounding area so that the activated frame 158 may be distinguished.

The activated frame 158 may also be partially transparent such that at least a portion (or portions) of the imaging screen 150 that appears below the activated frame 158 may be visible (e.g., perceived, identified, recognized) through the activated frame 158 by the operator. For example, the anatomical feature 172 of the acquired image 170 may be visible through the partially transparent activated frame 158. For illustrative purposes, portions of the acquired image 170 that appear behind the activated frame 158 have been identified with dashes. When the acquired image 170 includes a real-time image, the anatomical features 172 may appear to move behind the activated frame 158.

When the user-selectable element 161 is selected, the activated frame 158 may appear immediately or may appear to "pop-up" from a designated location. In particular embodiments, the activated frame 158 may appear to slide from the side 151 of the display area 157 over the acquired image 170. In such cases, the activated frame may be referred to as an activated tray. As the activated tray 158 slides over the acquired image, the activated tray 158 may be transparent to the anatomical feature 172 and the acquired image 170 as the activated tray 158 slides over.

In the illustrated embodiment, the display area 157 is a two-dimensional surface such that the activated frame 158 and the imaging screen 150 cannot be positioned spatially relative to each other such that one or the other is closer to the operator. It is understood that when a graphical element is described as being positioned over, on top of, behind, below, and like terms, the graphical elements only appear to be positioned as such. Instead, the pixels in the display area 157 of the display device 118 are configured to provide this appearance. For example, when the imaging screen 150 appears to be located under the activated frame 158, the pixels in the display area 157 are instructed to modify the corresponding light intensities to provide the appearance that the activated frame 158 is located over the elements of the imaging screen 150 (e.g., the acquired image 170). The pixels may also be configured to give the appearance that the activated frame 158 is partially transparent such that the anatomical structure 172 of the acquired image 170 is visible through the activated frame 158.

The activated frame 158 may have different areas or portions with different transparency levels. For example, the activated frame 158 includes the data fields 180, one or more wall regions 181, and a user-selectable element 182. The activated frame 158 may also include text 183. The wall regions 181 may represent a back space or background that facilitates distinguishing other elements of the activated frame 158. In some embodiments, the data fields 180 and the user-selectable element 182 may be less transparent than the wall regions 181 (e.g., may more effectively block the acquired image 170). In this manner, the wall regions 181 may facilitate distinguishing the data fields 180 from each other because the wall regions 181 have different transparencies.

In particular embodiments, the data fields 180 may appear solid or opaque relative to other portions or areas of the activated frame 158 such that the imaging screen 150 is not visible through the data fields 180. For example, the data fields 180 may be a solid white color as shown in FIG. 3. Thus, the activated frame 158 may include portions that extend over the acquired image 158 and that have different transparency levels.

In some embodiments, the method 200 may include receiving at 210 a user input for entering data into data fields 180 of the activated frame 158. The data fields 180 are configured to receive user inputs. In the illustrated embodiment, the data fields 180 are configured to receive textual inputs from the operator. More specifically, the data fields 180 may prompt the operator to enter a patient identification number, first and last names of the patient, demographic information regarding the patient, vital statistics of the patient, comments for the imaging session, and the like. Although the data fields 180 are configured to receive textual inputs, other user inputs may be received, such a selection from a number of options in a menu. However, in other embodiments, the activated frame 158 may only present information to the operator and not be capable of receiving user inputs.

In some embodiments, the activated frame 158 may prompt the operator to change operational settings of the ultrasound system 100. By way of example only, the operational settings may affect at least one of acquisition of a medical image during the imaging session or how information is displayed to the operator during the imaging session. The operational settings may affect (e.g., produce an effect upon, influence, determine, etc.) the image acquisition when the operational settings affect how the image data is obtained from the patient or how the medical image is derived from the image data. For example, the operational settings may affect the ultrasound signals that are transmitted into the patient's body and/or the reception of the ultrasound signals. The operational settings may also affect the acquisition when the operational settings affect how the received ultrasound signals are processed and/or analyzed to form the medical image. The operational settings may include imaging parameters that affect the medical image (e.g., type of medical image, quality of the medical image, orientation or view of the volume of interest (VOI) in the medical image, or a size and shape of the volume of interest in the medical image). Specific examples of imaging parameters may include one or more of a depth of field of view in an ultrasound image, the gain of an ultrasound image, the frequency of ultrasound signals emitted by the probe, a focal position of the ultrasound waves emitted by the probe, and the imaging mode used to obtain the ultrasound image (e.g., B-mode, color, pulsed wave ("PW"), power Doppler Imaging ("PDI"), or M-mode imaging).

At 212, the user interface 122 (FIG. 1) may receive a user input for removing the activated frame 158 from the imaging screen 150. For example, the operator may select the user-selectable element 161 again to remove the activated frame 158 or the operator may select an inactive portion of the display area 157 to remove the activated frame 158. An inactive portion may be a portion of the display area 157 that appears to be behind the activated frame 158. For instance, in FIG. 3, the inactive portion of the display area 157 may be any portion of the display area 157 other than the activated frame 158.

In other embodiments, the activated frame 158 may be automatically removed by the system controller 115 after the operator executes or performs a designated operation. For example, the activated frame 158 may be automatically removed after the last data field is entered or after the operator has selected an option from a drop-down menu.

In some embodiments, more than one activated frame may overlap one another. For example, a first activated frame may appear to be on top of a second activated frame and the acquired image 170 may appear to be at the bottom. In such cases, the first activated frame may be partially transparent such that the second activated frame and the acquired image 170 are visible. In other embodiments, the second activated frame may not be visible through the first activated frame where the first and second activated frames should overlap, but the acquired image may be visible through the first activated frame. In other embodiments, the acquired image may not be visible through the first and second activated frames where the first and second activated frames overlap each other.

Thus, embodiments described herein may permit the operator to view the acquired image 170 while also viewing and interacting with the activated frame 158 (e.g., executing non-imaging tasks, such as data entry). As one example, in some embodiments, the operator may use one hand to control the ultrasound probe and another hand to interact with the user interface. In such embodiments in which the acquired image is a real-time image, the operator may recognize while entering user inputs into the activated frame 158 that the volume of the subject being imaged has changed because the probe has inadvertently moved and/or the subject has moved.

Figure 4:
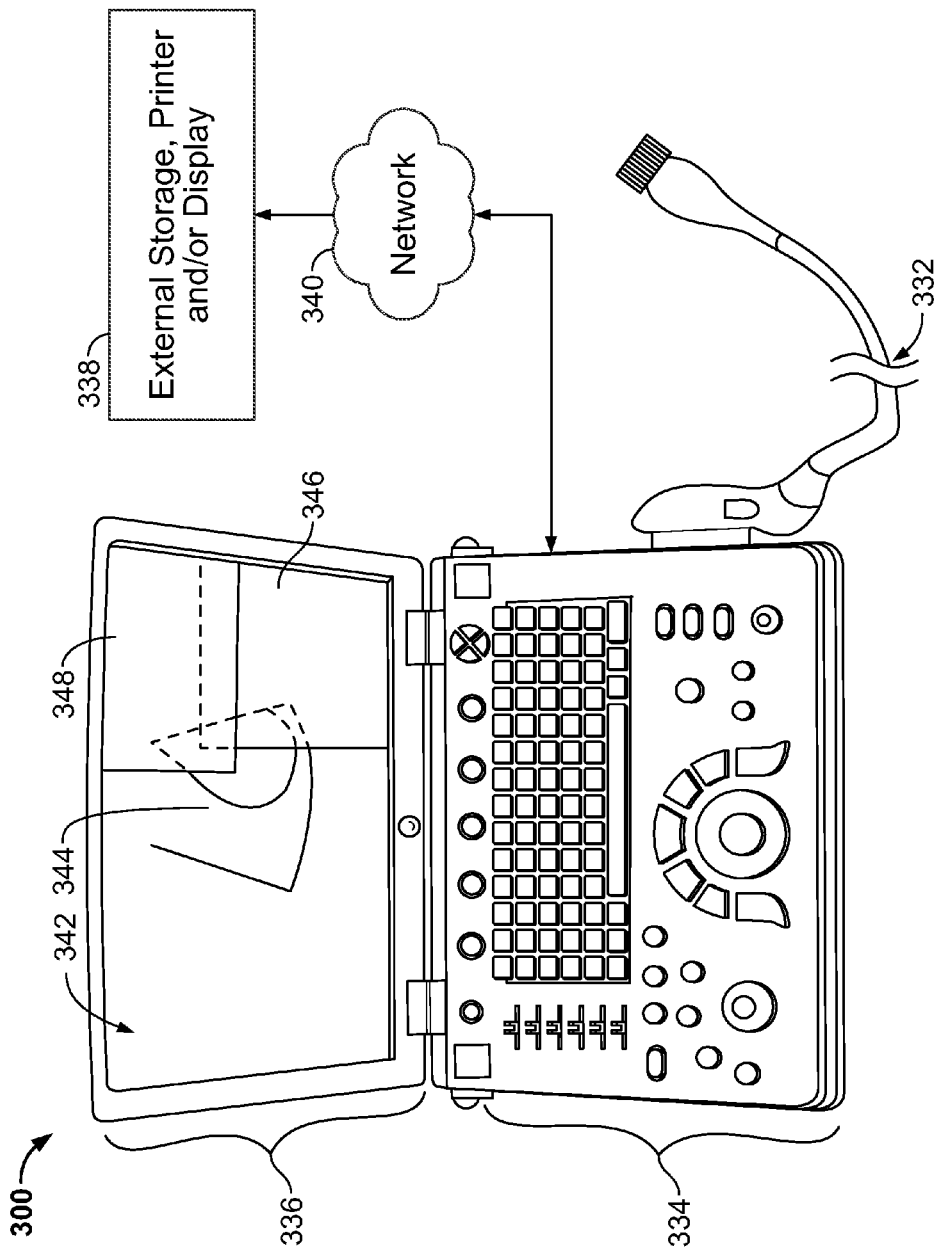
FIG. 4 illustrates an ultrasound system in which various embodiments may be implemented.

FIG. 4 illustrates a portable ultrasound system 300 having an ultrasound transducer 332 that may be configured to acquire ultrasonic data. For example, the ultrasound transducer 332 may have a 2D array of acoustic elements. A user interface 334 (that may also include an integrated display 336) is provided to receive commands from an operator. As used herein, "portable" includes a handheld or hand-carried device that may be carried in a person's hand, pocket, briefcase-sized case, or backpack. For example, the ultrasound system 300 may be a hand-carried device having a size of a typical laptop computer. The integrated display 336 (e.g., an internal display) is configured to display, for example, one or more medical images. The ultrasonic data may be sent to an external device 338 via a wired or wireless network 340 (or direct connection, for example, via a serial or parallel cable or USB port). In some embodiments, the external device 338 may be a computing system (e.g., computer, server, and the like).

The display 336 may be configured to show an imaging screen and a transparent activated frame(s), such as those described above. For instance, the display 336 includes a display area 342 that is configured to display an acquired ultrasound image 344. In the illustrated embodiment, a plurality of activated frames 346, 348 are shown and appear to be overlapping each other with the activated frame 348 closest to the operator and, therefore, more viewable to the operator. In some embodiments, when multiple activated frames overlap each other in the display area 342, the overlapped portions may have different transparencies than the non-overlapped portions.

Figure 5:
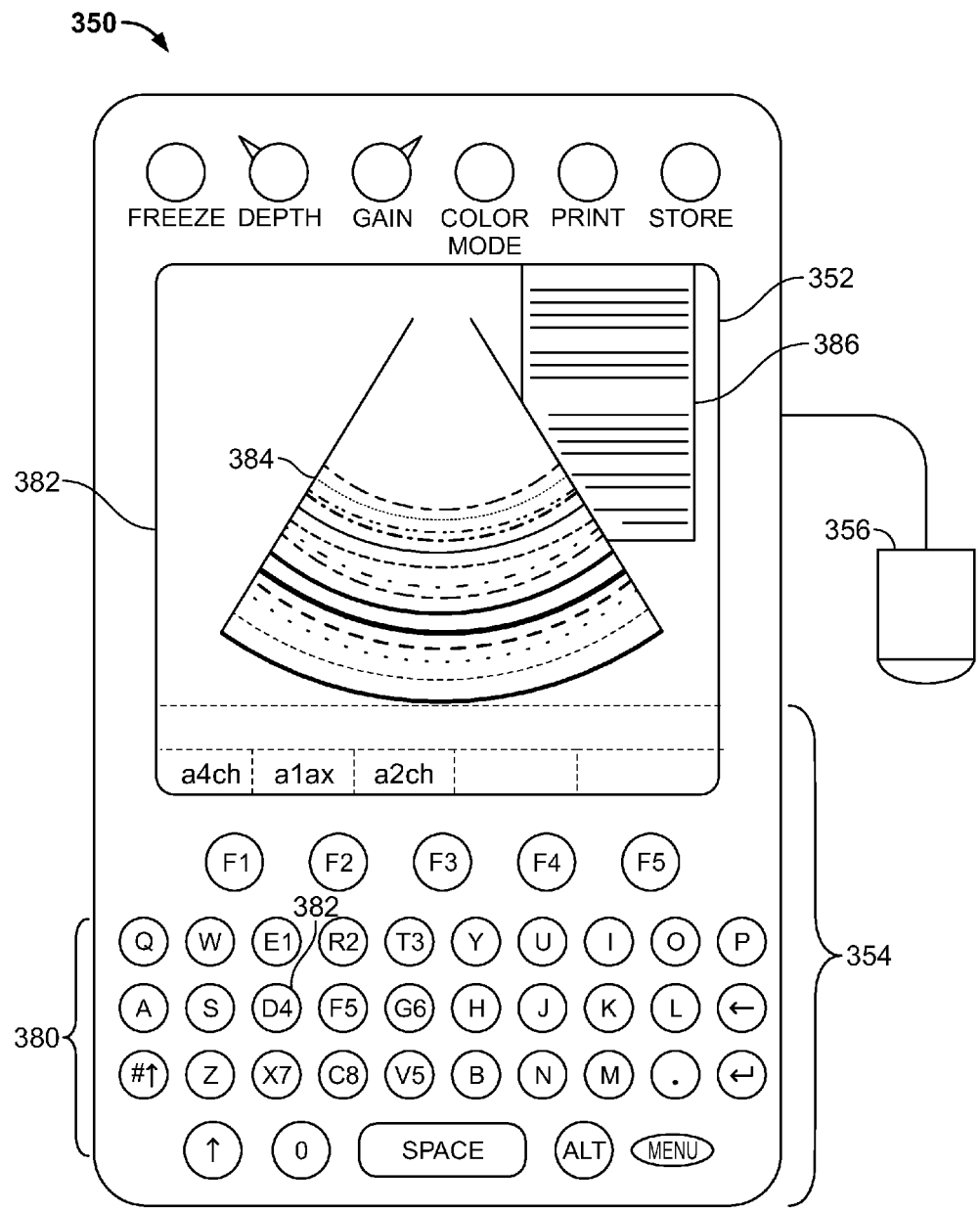
FIG. 5 illustrates a portable ultrasound imaging system in which various embodiments may be implemented.

FIG. 5 illustrates a portable hand-carried or pocket-sized ultrasound imaging system 350 wherein a display 352 and a user interface 354 form a single unit. By way of example, the pocket-sized ultrasound imaging system 350 may be a personal communication device, such as a smartphone or tablet. By way of example, the personal communication device may be dimensioned to be less than 3 inches wide, less than 4 inches in length, and less than 0.5 inches in depth, less than 8 ounces in weight. The portable ultrasound imaging system 350 generally includes the display 352, user interface 354, which may or may not include a keyboard-type interface and an input/output (I/O) port for connection to a scanning device, for example, and an ultrasound transducer 356. The display 352 may be, for example, a 320×320 pixel color LCD display (on which a medical image 390 may be displayed). A typewriter-like keyboard 380 of buttons 382 may optionally be included in the user interface 354. In other embodiments, the display 352 may be larger and a virtual keyboard may be shown.

In FIG. 5, the display 352 includes a display area 382 that includes an acquired image 384 and an activated frame 386. In some embodiments, instead of the activated frame 386 being removed from the display area 382, the activated frame 386 may appear to be moved behind the acquired image 384. To move the activated frame 386 to the front such that the activated frame 386 is more viewable, the operator may press or otherwise select the activated frame 386.

Figure 6:
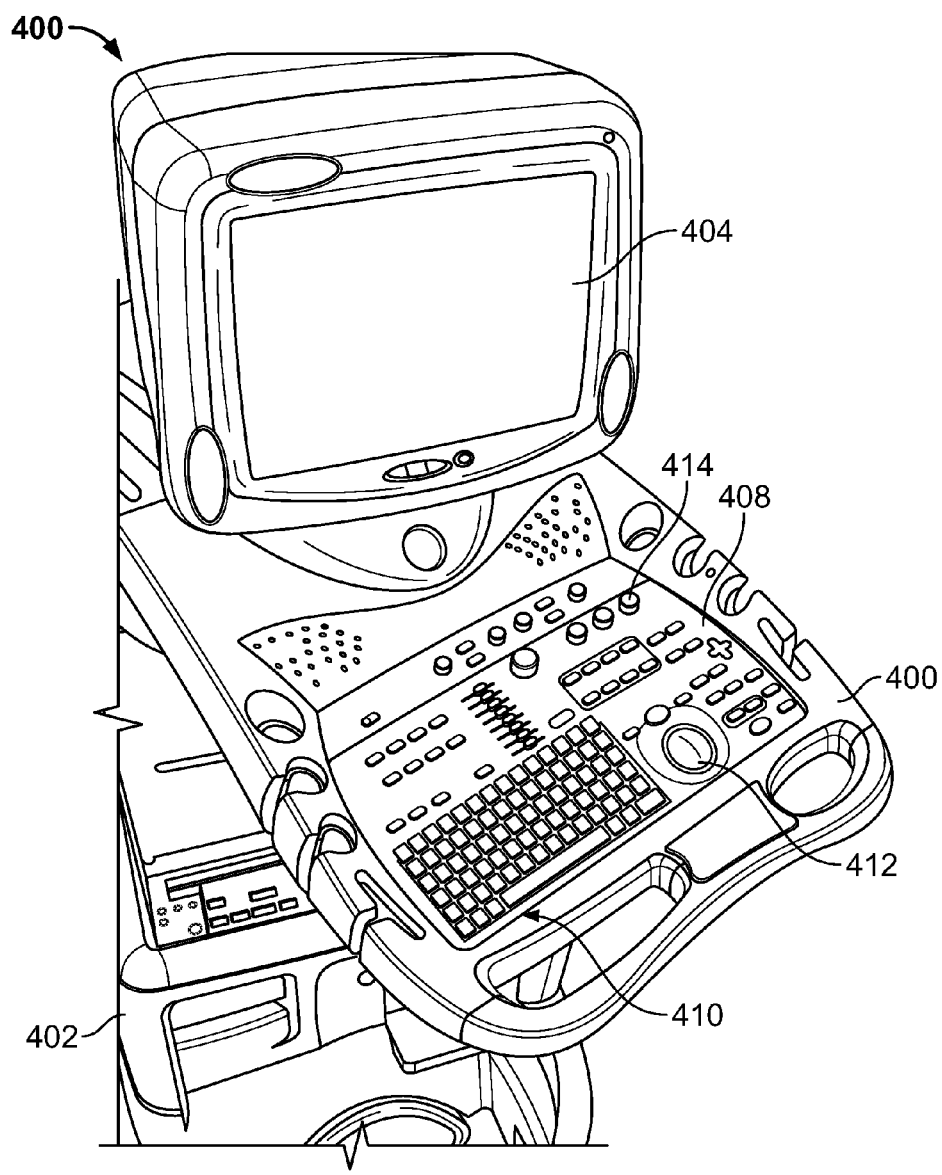
FIG. 6 illustrates a console-type ultrasound imaging system in which various embodiments may be implemented.

FIG. 6 illustrates an ultrasound imaging system 400 provided on a movable base 402. The portable ultrasound imaging system 400 may also be referred to as a cart-based system. A display 404 and user interface 406 are provided and it should be understood that the display 404 may be separate or separable from the user interface 406. The user interface 406 may optionally be a touchscreen, allowing the operator to select options by touching displayed graphics, icons, and/or the like.

The user interface 406 also includes control buttons 408 that may be used to control the portable ultrasound imaging system 400 as desired or needed, and/or as typically provided. The user interface 406 provides multiple interface options that the user may physically manipulate to interact with ultrasound data and other data that may be displayed, as well as to input information and set and change scanning parameters and viewing angles, etc. For example, a keyboard 410, trackball 412 and/or multi-function controls 414 may be provided.

It should be noted that although one or more embodiments may be described in connection with an ultrasound system, the embodiments described herein are not limited to ultrasound systems. In particular, one or more embodiments may be implemented in connection with different types of medical imaging systems. Examples of such medical imaging systems include a magnetic resonance imaging (MRI) system, computed tomography (CT) system, positron emission tomography (PET) system, a PET/CT system, and single photon emission computed tomography (SPECT) system. In such embodiments, the acquired images may be MRI images, CT images, PET images, PET/CT images, and SPECT images.

At least one technical effect of one or more embodiments described herein includes an improved workflow in which the operator experiences smoother transitions between different screens. One or more embodiments may also include an improved workflow that allows the operator to be more cognizant of the acquired image while interacting with different frames or windows. More specifically, while the primary attention of the operator may be focused on an activated window, the background display of the acquired image may enable the operator to more quickly or easily re-establish where he or she is in the workflow when he or she returns to the acquired image.

As used herein, the term "computing system" or "system controller" may include any processor-based or microprocessor-based systems including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computing system" or "system controller."

Sets of instructions may include various commands that instruct the computing system or system controller as a processing machine to perform specific operations such as the methods and processes described herein. The set of instructions may be in the form of a software program or module. The software may be in various forms such as system software or application software. Further, the software may be in the form of a collection of separate programs, a program module (or module) within a larger program, or a portion of a program module. The software also may include modular programming in the form of object-oriented programming. The processing of input data by the processing machine may be in response to user commands, or in response to results of previous processing, or in response to a request made by another processing machine. The program is configured to run on both 32-bit and 64-bit operating systems. A 32-bit operating system like Windows XP™ can only use up to 3 GB bytes of memory, while a 64-bit operating system like Window's Vista™ can use as many as 16 exabytes (16 billion GB). In some embodiments, the program is configured to be executed on a Linux-based system.

As used herein, the terms "software" and "firmware" are interchangeable, and include any computer program stored in memory for execution by a computing system, including RAM memory, ROM memory, EPROM memory, EEPROM memory, and non-volatile RAM (NVRAM) memory. The above memory types are exemplary only, and are thus not limiting as to the types of memory usable for storage of a computer program.

In one embodiment, an ultrasound imaging system is provided that includes a user interface configured to receive user inputs from an operator during an imaging session. The user interface includes a display device having a display area. The system also includes an image-processing module that is configured to receive ultrasound signals from a diagnostic probe and process the signals to generate ultrasound images. The system may also include a workflow module that is configured to display, concurrently, an acquired image of the ultrasound images and a user-selectable element in the display area. The acquired image includes an anatomical feature of a subject. The workflow module is configured to display an activated frame over the acquired image in the display area when the user-selectable element is selected by the operator. The activated frame appears partially transparent such that the anatomical feature is visible through the activated frame.

In some embodiments, the activated frame includes data fields configured to receive a textual input from the operator. The data fields may appear solid such that the acquired image is not visible through the data fields. Adjacent data fields may also be separated by a wall region. The wall region and the data fields may have different transparency levels.

In some aspects, the display device includes a touch-sensitive display that includes the display area. The user-selectable element is configured to be selected by the operator through a touch.

In some aspects, the system includes a device housing that is dimensioned to be carried by an adult individual. The ultrasound imaging system constituting a portable communication device.

In some aspects, the activated frame may appear to slide from a side of the display area. The anatomical feature of the subject appearing through the activated frame as the activated frame slides over the anatomical feature.

In yet another embodiment, a tangible non-transitory computer readable medium, excluding signals, is provided that is programmed to instruct a computing system to receive user inputs from an operator at a user interface of a medical imaging system. The user inputs include identification data that identifies the operator. The computing system is also instructed to receive, at the medical imaging system, a user profile from a profile-storage system that is at a distinct location with respect to the medical imaging system. The user profile includes predetermined operational settings that are associated with the operator. The computing system is also instructed to load the predetermined operational settings into the medical imaging system, wherein each of the predetermined operational settings is selected from a plurality of potential operational settings that control operation of the medical imaging system. The computing system is also instructed to image a patient during an imaging session. The predetermined operational settings affect at least one of acquisition of a medical image during the imaging session or information that is displayed to the operator during the imaging session.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of various embodiments, they are by no means limiting and are only example embodiments. Many other embodiments will be apparent to those of skill in the art upon reviewing the above description. The scope of the present application should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An ultrasound imaging system comprising:
   a user interface configured to receive user inputs from an operator during an imaging session, the user interface including a display device having a display area;
   the system including one or more processors that are configured to:
   receive ultrasound signals from a diagnostic probe and process the signals to generate ultrasound images; and
   display, concurrently, an acquired image of the ultrasound images and a user-selectable element in the display area, the acquired image including an anatomical feature of a subject, the one or more processors being configured to display an activated frame over the acquired image in the display area when the user-selectable element is selected by the operator, the activated frame appearing partially transparent such that the anatomical feature is visible through the activated frame, wherein the activated frame includes a data field that is configured to receive a user input entered by the operator as the acquired image is located under the data field, wherein the activated frame appears over the acquired image in response to the user-selectable element being selected by the operator, the activated frame covering an area of the acquired image, the user interface configured to remove the activated frame from the area in response to a user action, wherein the area of the acquired image is not covered after the activated frame is removed from the area.

2. The system of claim 1, wherein the data field is configured to receive a textual input from the operator while the acquired image is located under the data field and the anatomical feature is visible through the activated frame.

3. The system of claim 1, wherein the data field appears solid such that the acquired image is not visible through the data field while the anatomical feature is visible through the activated frame.

4. The system of claim 1, wherein the activated frame includes a plurality of the data fields and wherein adjacent data fields are separated by a wall region, the wall region and the data fields having different transparency levels.

5. The system of claim 1, wherein the display device includes a touch-sensitive display that includes the display area, the user-selectable element configured to be selected by the operator with a touch.

6. The system of claim 1, wherein the acquired image is at least one of a single ultrasound image frame, real-time ultrasound images, or a recorded cine movie.

7. An ultrasound imaging system comprising:
a user interface configured to receive user inputs from an operator during an imaging session, the user interface including a display device having a display area;
the system including one or more processors configured to:
receive ultrasound signals from a diagnostic probe and process the signals to generate ultrasound images; and
display, concurrently, an acquired image of the ultrasound images and a user-selectable element in the display area, the acquired image including an anatomical feature of a subject, the one or more processors configured to display an activated frame over the acquired image in the display area when the user-selectable element is selected by the operator, the activated frame appearing partially transparent such that the anatomical feature is visible through the activated frame, wherein the activated frame slides from a side of the display area, the anatomical feature of the subject appearing through the activated frame as the activated frame slides over the anatomical feature, wherein the activated frame appears over the acquired image in response to the user-selectable element being selected by the operator, the activated frame covering an area of the acquired image, the user interface configured to remove the activated frame from the area in response to a user action, wherein the area of the acquired image is not covered after the activated frame is removed from the area.

8. The system of claim 1, wherein the activated frame is a first activated frame, the workflow module configured to concurrently display a second activated frame, wherein the second activated frame appears partially transparent such that the anatomical feature is visible through the second activated frame.

9. A method of imaging a subject using an ultrasound imaging system, the method comprising:
processing ultrasound signals to generate ultrasound images, the ultrasound images including an acquired image, the acquired image including an anatomical feature of a subject;
concurrently displaying the acquired image and a user-selectable element in a display area;
displaying an activated frame over the acquired image in the display area when the user-selectable element is selected by the operator, the activated frame appearing partially transparent such that the anatomical feature is visible through the activated frame, wherein the activated frame includes a data field that is configured to receive a user input entered by the operator as the acquired image is located under the data field, wherein the method is performed using one or more processors, wherein the activated frame appears over the acquired image in response to the user-selectable element being selected by the operator, the activated frame covering an area of the acquired image; and
removing the activated frame from the area in response to a user action, wherein the area of the acquired image is not covered after the activated frame is removed from the area.

10. The method of claim 9, wherein the data field is configured to receive a textual input from the operator while the acquired image is located under the data field and the anatomical feature is visible through the activated frame.

11. The method of claim 9, wherein the data field appears solid such that the acquired image is not visible through the data field while the anatomical feature is visible through the activated frame.

12. The method of claim 9, wherein the activated frame includes a plurality of the data fields and wherein adjacent data fields are separated by a wall region, the wall region and the data fields having different transparency levels.

13. The method of claim 9, wherein the activated frame slides from a side of the display area when the user-selectable element is selected by the operator, the anatomical feature of the subject appearing through the activated frame as the activated frame slides over the anatomical feature.

14. The system of claim 1, wherein the activated frame appears over the acquired image in response to the user-selectable element being selected by the operator, the activated frame covering a majority of the acquired image.

15. The system of claim 1, wherein the activated frame appears over the acquired image in response to the user-selectable element being selected by the operator, the activated frame covering a center of the acquired image.

16. The system of claim 1, wherein the user action comprises a user input for removing the activated frame.

17. The system of claim 1, wherein the data field has a field area that is configured to receive the user input, the activated frame also including a wall region that at least partially defines the field area, the wall region and the field area having different transparency levels when positioned over the acquired image such that the acquired image is more visible through the wall region compared to the field area.

18. The system of claim 1, wherein the data field is a first data field and the activated frame includes a second data field configured to receive a user input from the operator and a wall region that separates the first and second data fields, the wall region and the first and second data fields having different transparency levels when positioned over the acquired image such that the acquired image is more visible through the wall region compared to the first and second data fields.

19. The system of claim 1, wherein the acquired image is a real-time image that is visible through the activated frame such that the anatomical feature may move when under the activated frame.

20. The system of claim 1, wherein the activated frame covers only a portion of the display area.

21. The system of claim 1, wherein the user action comprises executing or performing a designated operation.

22. The system of claim 7, wherein the user action comprises a user input for removing the activated frame.

23. The system of claim 7, wherein the user action comprises executing or performing a designated operation.

24. The method of claim 9, wherein the user action comprises a user input for removing the activated frame.

25. The method of claim 9, wherein the user action comprises executing or performing a designated operation.

* * * * *